(12) United States Patent
Elder et al.

(10) Patent No.: US 9,500,616 B2
(45) Date of Patent: Nov. 22, 2016

(54) MULTI-ORIENTATION TEST STRIP

(71) Applicant: Cilag GmbH International, Zug (CH)

(72) Inventors: David Elder, Inverness (GB); Steven Setford, Inverness (GB); Allan Faulkner, Inverness (GB); Ryan Walsh, Douglassville, PA (US)

(73) Assignee: Cilag GmbH International, Zug (CH)

( * ) Notice: Subject to any disclaimer, the term of this patent is extended or adjusted under 35 U.S.C. 154(b) by 389 days.

(21) Appl. No.: 14/138,671

(22) Filed: Dec. 23, 2013

(65) Prior Publication Data

US 2015/0177175 A1   Jun. 25, 2015

(51) Int. Cl.
*G01N 27/327* (2006.01)
*G01N 27/30* (2006.01)

(52) U.S. Cl.
CPC ........ *G01N 27/307* (2013.01); *G01N 27/3272* (2013.01)

(58) Field of Classification Search
CPC ............ C12Q 1/00; C12Q 1/02; C12Q 1/34; C12Q 1/54; G01N 27/327; G01N 27/3272; G01N 27/48; G01N 27/26; G01N 27/307; G01N 33/487; A61B 5/05; A61B 5/14532
See application file for complete search history.

(56) References Cited

U.S. PATENT DOCUMENTS

| | | |
|---|---|---|
| 6,491,870 B2 | 12/2002 | Patel et al. |
| 6,780,645 B2 | 8/2004 | Hayter et al. |
| 6,881,578 B2 | 4/2005 | Otake |
| 7,090,984 B2 | 8/2006 | Hashimoto et al. |
| 7,144,485 B2 | 12/2006 | Hsu et al. |
| 7,244,394 B2 | 7/2007 | Carney et al. |
| 7,875,461 B2 | 1/2011 | Docherty et al. |
| 7,919,331 B2 | 4/2011 | Geisberg |
| 8,221,685 B2 | 7/2012 | Feldman et al. |
| 8,394,246 B2 | 3/2013 | Celentano et al. |
| 8,481,278 B2 | 7/2013 | Geiger et al. |
| 8,511,147 B2 | 8/2013 | Wang |
| 2002/0168290 A1* | 11/2002 | Yuzhakov ............ A61B 5/1411 422/400 |
| 2003/0042150 A1 | 3/2003 | Ryu et al. |
| 2005/0258035 A1* | 11/2005 | Harding ................ C12Q 1/004 204/403.01 |
| 2006/0161078 A1* | 7/2006 | Schraga ............... A61B 5/1411 600/583 |
| 2007/0227911 A1 | 10/2007 | Wang et al. |
| 2008/0053194 A1 | 3/2008 | Ahmad et al. |

(Continued)

FOREIGN PATENT DOCUMENTS

| | | |
|---|---|---|
| EP | 2597462 A1 | 5/2013 |
| WO | 2006070199 | 7/2006 |
| WO | 2009076244 | 6/2009 |
| WO | 2013076134 | 5/2013 |

OTHER PUBLICATIONS

International Search Report and Written Opinion issued in related International Patent Application No. PCT/US2014/071805, dated Jun. 1, 2015, 16 pages.

(Continued)

*Primary Examiner* — Jennifer Dieterle

(57) ABSTRACT

A test strip having conductive surfaces separated by a spacer layer, wherein the spacer layer is comprised of sections forming a plurality of sample chambers that enable the test strip to be inserted into a test meter in a number of possible orientations. The test strip also includes electrical contact pads on opposing sides thereof such that the test meter may separately engage the contact pads depending on the insertion orientation.

3 Claims, 4 Drawing Sheets

(56) References Cited

U.S. PATENT DOCUMENTS

| | | |
|---|---|---|
| 2009/0301899 A1 | 12/2009 | Hodges et al. |
| 2010/0051455 A1 | 3/2010 | Wooldridge et al. |
| 2011/0040208 A1 | 2/2011 | McMinn et al. |
| 2011/0077490 A1 | 3/2011 | Simpson et al. |
| 2012/0234487 A1* | 9/2012 | Wang ................ B01L 3/502715 156/268 |
| 2013/0146478 A1 | 6/2013 | Iyengar et al. |

OTHER PUBLICATIONS http://www.firstoptionmedical.com/Ascensia-Microfill-Blood-Glucose-Test-Strips-p/15005.htm, First Option Medical. Custom Shape for easy handling. Oct. 11, 2013.

* cited by examiner

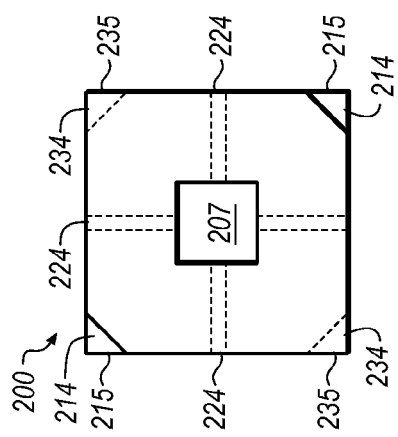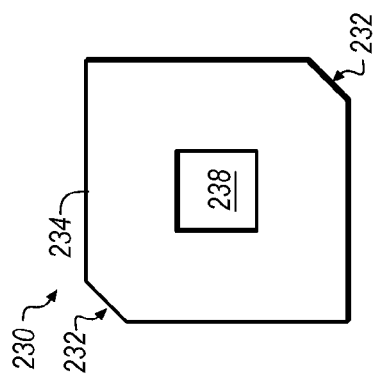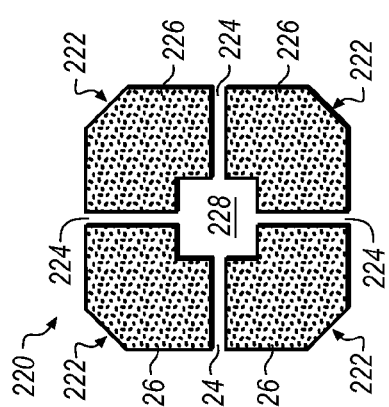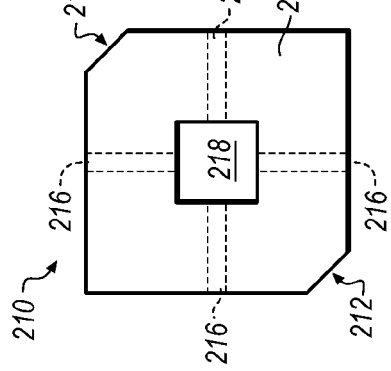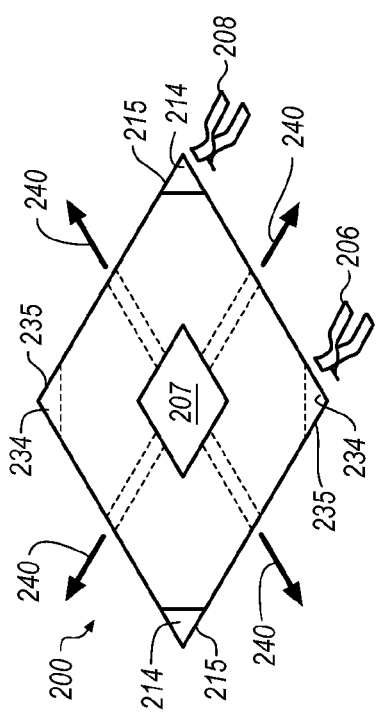

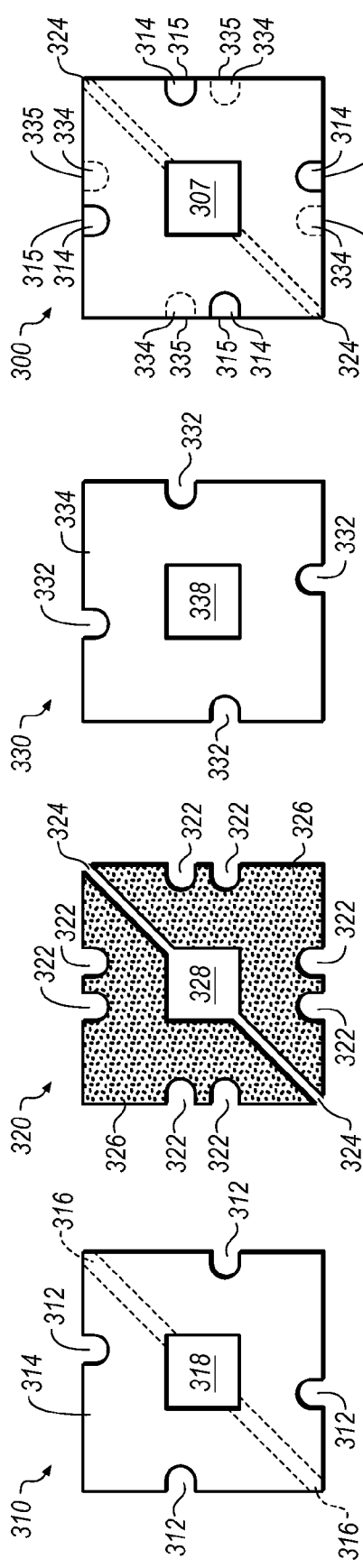

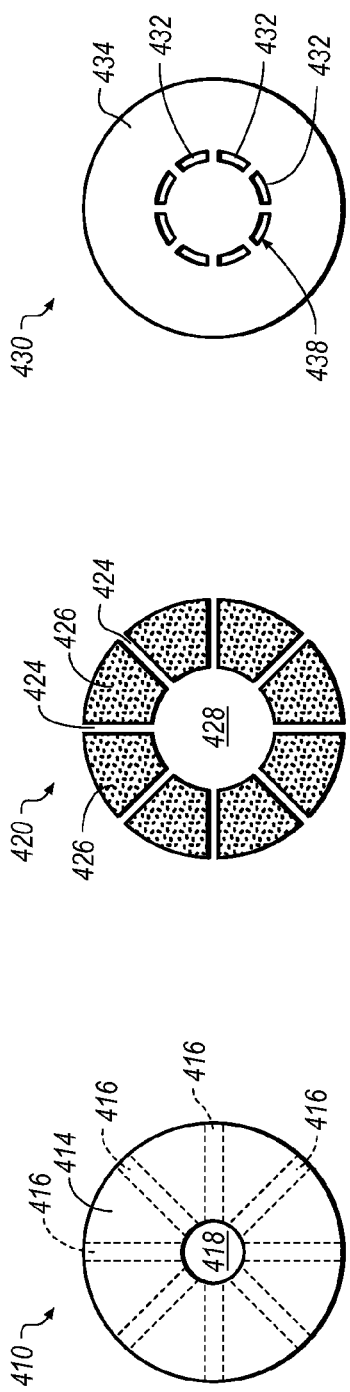
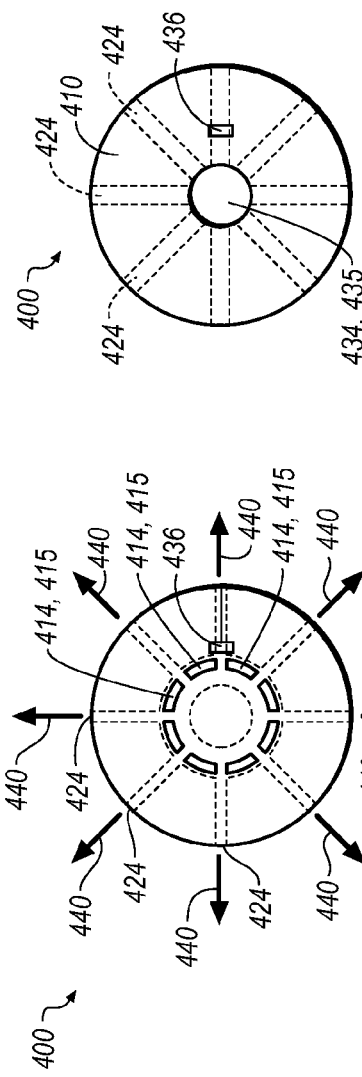

MULTI-ORIENTATION TEST STRIP

TECHNICAL FIELD

This application generally relates to the field of blood analyte measurement systems and more specifically to a test strip that can be inserted into a blood analyte measurement system in any of several different orientations.

BACKGROUND

Blood glucose measurement systems typically comprise a meter that is configured to receive a biosensor, usually in the form of a test strip. Because many of these systems are portable, and testing can be completed in a short amount of time, patients are able to use such devices in the normal course of their daily lives without significant interruption to their personal routines. A person with diabetes may measure their blood glucose levels several times a day as a part of a self management process to ensure glycemic control of their blood glucose within a target range.

There currently exist a number of available portable electronic analyte measurement devices (i.e., meters) that are designed to automatically activate upon insertion of a test strip. Electrical contacts, or prongs, in the meter establish connections with contact pads on the test strip while a microcontroller in the meter determines, based on electrical signals from the test strip, whether the test strip is properly inserted. Unless the test strip is inserted in a proper orientation, however, the device will not activate or, in addition, it may display an error message until the test strip is properly reinserted. This effort may present difficulty for some users who might struggle to correctly orient the test strip prior to insertion, particularly if the test strip is difficult to handle.

It would be beneficial to have a test strip that could be inserted into a test meter in a multitude of orientations so that the user does not have to focus on strip orientation when using the test meter. Such a test strip would also reduce the amount of training required for a user to learn to properly operate the test meter.

BRIEF DESCRIPTION OF THE DRAWINGS

The accompanying drawings, which are incorporated herein and constitute part of this specification, illustrate presently preferred embodiments of the invention, and, together with the general description given above and the detailed description given below, serve to explain features of the invention (wherein like numerals represent like elements).

FIGS. 2A-C illustrate three layers of an exemplary test strip for use in the analyte measurement system of FIGS. 1A and 1B;

FIG. 2D is a top view of the exemplary test strip assembled from the layers illustrated in FIGS. 2A-C;

FIG. 2E is a perspective view of the exemplary test strip of FIG. 2D in relation to electrical contacts of a test meter;

FIGS. 3A-C illustrate three layers of another exemplary test strip;

FIG. 3D is a top view of the exemplary test strip assembled from the layers illustrated in FIGS. 3A-C;

FIG. 3E is a perspective view of the exemplary test strip of FIG. 3D in relation to electrical contacts of a test meter;

FIGS. 4A-C illustrate three layers of yet another exemplary test strip; and

FIGS. 4D-E are a top view and a bottom view, respectively, of the exemplary test strip assembled from the layers illustrated in FIGS. 4A-C.

MODES OF CARRYING OUT THE INVENTION

The following detailed description should be read with reference to the drawings, in which like elements in different drawings are identically numbered. The drawings, which are not necessarily to scale, depict selected embodiments and are not intended to limit the scope of the invention. The detailed description illustrates by way of example, not by way of limitation, the principles of the invention. This description will clearly enable one skilled in the art to make and use the invention, and describes several embodiments, adaptations, variations, alternatives and uses of the invention, including what is presently believed to be the best mode of carrying out the invention.

As used herein, the terms "patient" or "user" refer to any human or animal subject and are not intended to limit the systems or methods to human use, although use of the subject invention in a human patient represents a preferred embodiment.

The term "sample" means a volume of a liquid, solution or suspension, intended to be subjected to qualitative or quantitative determination of any of its properties, such as the presence or absence of a component or the concentration of a component, e.g., an analyte, etc. The embodiments of the present invention are applicable to human and animal samples of whole blood. Typical samples in the context of the present invention as described herein include blood, plasma, serum, suspensions thereof, and haematocrit.

The term "about" as used in connection with a numerical value throughout the description and claims denotes an interval of accuracy, familiar and acceptable to a person skilled in the art. The interval governing this term is preferably ±10%. Unless specified, the terms described above are not intended to narrow the scope of the invention as described herein and according to the claims.

Figure 1A:
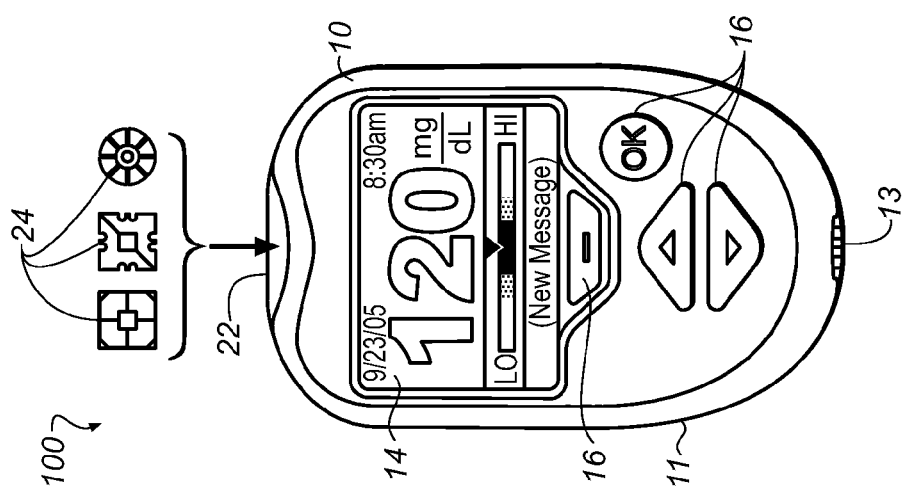
FIG. 1A illustrates a diagram of an exemplary analyte measurement system.

FIG. 1A illustrates an analyte measurement system 100 that includes an analyte meter 10. The analyte meter 10 is defined by a housing 11 that retains a plurality of components including a data management unit ("DMU") 140, FIG. 1B, and further includes a test strip port 22 provided on one side of the housing 11 that is appropriately sized for receiving a biosensor. According to one embodiment, the analyte meter 10 may be a hand-held blood glucose meter and the biosensor is provided in the form of a test strip 24 inserted into the test strip port 22 for performing blood glucose measurements. As discussed herein, the test strip 24 may be a multi-orientation test strip having one of a plurality of possible geometries and configurations. Each of the possible configurations define test strip designs that enable the strip 24 to be inserted into the test strip port 22 in a number of different orientations. The analyte meter 10 further includes a plurality of user interface buttons 16, and a display 14 as illustrated in FIG. 1A which are disposed on a front facing side of the housing 11. A predetermined number of glucose test strips 24 may be stored in the housing 11 and made accessible for use in blood glucose testing. The plurality of user interface buttons 16 are associated with the DMU 140, FIG. 1B, and can be configured to allow the entry of data, to prompt an output of data, to navigate menus presented on the display 14, and to initiate execution of commands. Output data can include values representative of analyte concentration presented on the display 14. Inputs from the user may be requested via prompts presented on the display 14 and responses thereto may initiate execution of commands by a processing unit of the meter 10 or the responses may be stored in a memory module of the analyte meter 10. Specifically and according to this exemplary embodiment, the user interface buttons 16 include markings, e.g., up-down arrows, text characters "OK", etc, which allow a user to navigate through the user interface presented on the display 14. Although the buttons 16 are shown herein as separate switches, a touch screen interface on display 14 with virtual buttons may also be utilized.

Figure 1B:
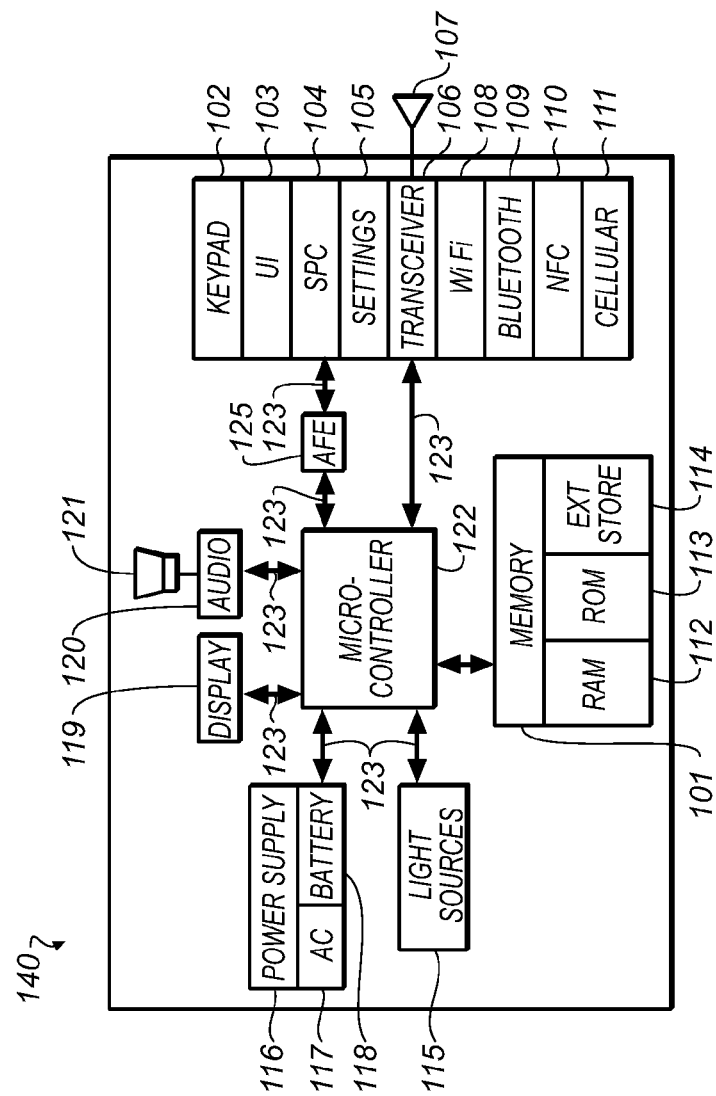
FIG. 1B illustrates a diagram of an exemplary processing system of the analyte measurement system of FIG. 1A.

The electronic components of the analyte measurement system 100 can be disposed on, for example, a printed circuit board situated within the housing 11 and forming the DMU 140 of the herein described system. FIG. 1B illustrates, in simplified schematic form, several of the electronic subsystems disposed within the housing 11 for purposes of this embodiment. The DMU 140 includes a processing unit 122 in the form of a microprocessor, a microcontroller, an application specific integrated circuit ("ASIC"), a mixed signal processor ("MSP"), a field programmable gate array ("FPGA"), or a combination thereof, and is electrically connected to various electronic modules disposed on, or connected to, the printed circuit board, as will be described below. The processing unit 122 is electrically connected to, for example, a test strip port connector 104 ("SPC") via an analog front end (AFE) subsystem 125. The AFE subsystem 125 is electrically connected to the strip port connector 104 during blood glucose testing. To measure a selected analyte concentration, the AFE subsystem 125 detects a resistance magnitude change across electrodes of analyte test strip 24 which indicates that a blood sample has been applied thereto, using a potentiostat. At a predetermined time after the blood sample has been applied to the test strip 24, a preset voltage waveform is applied across the sample via the electrodes which generates an electric current therethrough. The AFE subsystem 125 converts the electric current measurement into digital form for presentation on the display 14, as shown in FIG. 1A. Typically, the analyte concentration is displayed in units of milligrams per deciliter (mg/dl) or millimoles per liter (mmol/l). The processing unit 122 can be configured to receive input from the strip port connector 104, analog front end subsystem 125, and may also perform a portion of the potentiostat function and the current measurement function.

As noted, the analyte test strip 24 can be in the form of a test strip for measuring glucose concentration, or other analyte appropriate for monitoring of a biological condition, comprising a plurality of electrochemical cells, and/or sample chambers, of which various embodiments are described herein. The test strip 24 is defined by one or more nonporous, non-conducting substrates, or layers, onto which one or more electrodes, or conductive coatings may be deposited. These electrodes may function as working electrodes, reference electrodes, counter electrodes or combined counter/reference electrodes. Additional non-conducting layers may be applied in order to define the planar dimensions of the electrode structure(s). Test strip 24 can also include a plurality of electrical contact pads, where each electrode can be in electrical communication with at least one electrical contact pad, as described below in relation to FIGS. 2A-4E. Each of the foregoing features is described in greater detail herein. The strip port connector 104 can be configured to electrically interface to the electrical contact pads, using electrical contacts in the form of flexible conductive prongs, and form electrical communication with the electrodes. Test strip 24 further includes a reagent layer that is disposed over one or more electrodes within the test strip 24, including the working electrode. The reagent layer can include an enzyme and a mediator. Exemplary enzymes suitable for use in the reagent layer include glucose oxidase, glucose dehydrogenase (with pyrroloquinoline quinone co-factor, "PQQ"), and glucose dehydrogenase (with flavin adenine dinucleotide co-factor, "FAD"). Enzymes other than those used to determine glucose are also applicable, for example, lactate dehydrogenase for lactate, β-hydroxybutyrate dehydrogenase for β-hydroxybutyrate (ketone body). An exemplary mediator suitable for use in the reagent layer includes ferricyanide, which in this case is in the oxidized form. Other mediators may be equally applicable, depending upon the desired strip operating characteristics, for example, ferrocene, quinone or osmium-based mediators. The reagent layer can be configured to physically transform glucose in the applied sample into an enzymatic by-product and in the process generate an amount of reduced mediator (e.g., ferrocyanide) that is proportional to the glucose concentration of the sample. The electrode can then be used to apply the preset voltage waveform to the sample and to measure a concentration of the reduced mediator in the form of an electric current magnitude. In turn, microcontroller 122 can convert the measured current magnitude into a glucose concentration for presentation on the display 14. An exemplary analyte meter performing such current measurements is described in U.S. Patent Application Publication No. US 2009/0301899 A1 entitled "System and Method for Measuring an Analyte in a Sample", which is incorporated by reference herein as if fully set forth in this application.

A display module 119, which may include a display processor and display buffer, is electrically connected to the processing unit 122 over the electrical interface 123 for receiving and displaying output data, and for displaying user interface input options under control of processing unit 122. The structure of the user interface, such as menu options, is stored in user interface module 103 and is accessible by processing unit 122 for presenting menu options to a user of the blood glucose measurement system 100. An audio module 120 includes a speaker 121 for outputting audio data received or stored by the DMU 140. Audio outputs can include, for example, notifications, reminders, and alarms, or may include audio data to be replayed in conjunction with display data presented on the display 14. Such stored audio data can be accessed by processing unit 122 and executed as playback data at appropriate times. A volume of the audio output is controlled by the processing unit 122, and the volume setting can be stored in settings module 105, as determined by the processor or as adjusted by the user. Keypad module 102 receives inputs via user interface buttons 16, or a keypad, which are processed and transmitted to the processing unit 122 over the electrical interface 123. The processing unit 122 may have electrical access to a digital time-of-day clock connected to the printed circuit board for recording dates and times of blood glucose measurements, which may then be accessed, uploaded, or displayed at a later time as necessary.

The display 14 can alternatively include a backlight whose brightness may be controlled by the processing unit 122 via a light source control module 115. Similarly, the user interface buttons 16 may also be illuminated using LED light sources electrically connected to processing unit 122 for controlling a light output of the buttons. The light source module 115 is electrically connected to the display backlight and processing unit 122. Default brightness settings of all light sources, as well as settings adjusted by the user, are stored in a settings module 105, which is accessible and adjustable by the processing unit 122.

A memory module 101, that includes but are not limited to volatile random access memory ("RAM") 112, a non-volatile memory 113, which may comprise read only memory ("ROM") or flash memory, and a circuit 114 for connecting to an external portable memory device, for example, via a USB data port, is electrically connected to the processing unit 122 over an electrical interface 123. External memory devices may include flash memory devices housed in thumb drives, portable hard disk drives, data cards, or any other form of electronic storage devices. The on-board memory can include various embedded applications and stored algorithms in the form of programs executed by the processing unit 122 for operation of the analyte meter 10, as explained herein. On board memory can also be used to store a history of a user's blood glucose measurements including dates and times associated therewith. Using the wireless transmission capability of the analyte meter 10 or the data port 13, as described below, such measurement data can be transferred via wired or wireless transmission to connected computers or other processing devices.

A wireless module 106 may include transceiver circuits for wireless digital data transmission and reception via one or more internal digital antennas 107, and is electrically connected to the processing unit 122 over electrical interface 123. The wireless transceiver circuits may be in the form of integrated circuit chips, chipsets, programmable functions operable via processing unit 122, or a combination thereof. Each of the wireless transceiver circuits is compatible with a different wireless transmission standard. For example, a wireless transceiver circuit 108 may be compatible with the Wireless Local Area Network IEEE 802.11 standard known as WiFi. Transceiver circuit 108 may be configured to detect a WiFi access point in proximity to the analyte meter 10 and to transmit and receive data from such a detected WiFi access point. A wireless transceiver circuit 109 may be compatible with the Bluetooth Low Energy protocol and is configured to communicate with a Bluetooth Smart central device in proximity to the analyte meter 10. A wireless transceiver circuit 110 may be compatible with the near field communication ("NFC") standard and is configured to establish radio communication with, for example, another NFC compliant device in proximity to the analyte meter 10. A wireless transceiver circuit 111 may comprise a circuit for cellular communication with cellular networks and is configured to detect and link to available cellular communication towers.

A power supply module 116 is electrically connected to all modules in the housing 11 and to the processing unit 122 to supply electric power thereto. The power supply module 116 may comprise standard or rechargeable batteries 118 or an AC power supply 117 may be activated when the analyte meter 10 is connected to a source of AC power. The power supply module 116 is also electrically connected to processing unit 122 over the electrical interface 123 for supplying power thereto and so that processing unit 122 can monitor a power level remaining in a battery power mode of the power supply module 116.

FIGS. 2A-2E illustrate an exemplary embodiment of a substantially flat (planar), rectangular test strip 200 that may be used for analyte measurement when the test strip 200 is inserted into a test strip port 22 of the analyte meter 100 in either of at least four (4) orientations wherein the test strip 24 is rotated within the plane defined by the test strip 200. With reference to FIGS. 2A-2C, the test strip 200 is generally defined by three layers herein referred to as a bottom layer 210, a top layer 230, and a spacer layer 220 therebetween, of the fully assembled test strip 200. The top and bottom layers, 230, 210, respectively, each define a substrate base and are made from an inert (non-conducting) support or backing material on which has been deposited, such as by sputtering, screen-printing, flexo printing, gravure printing, or other means, a conductive material which forms the working, reference, counter or combined reference/counter electrodes of the formed electrochemical test strip. The inert backing material is sufficiently rigid to provide adequate structural support to each of the formed electrodes and the test strip as a whole. Such suitable materials include plastics (e.g., PET, PETG, polyimide, polycarbonate, polyester) silicon, ceramic, glass, and the like. The conductive material is preferably either a metal, where metals of interest can include palladium (Pd), gold (Au), platinum, silver, iridium, doped iridium tin oxide, indium tin oxide, or a non-metal including include carbon, doped carbon, and the like. Similar, as well as dissimilar, metals may be used, i.e. Au—Au or Au—Pd, on the top and bottom layers, 230, 210.

The layers 210, 230 according to this specific embodiment may be fabricated from a sheet of polyester having the conductive coating sputtered on one side thereon. With respect to the bottom layer 210, a palladium coating 214 may be sputtered on the sheet of polyester to form the conductive coating on an inward facing side (after assembly) of the bottom layer 210. The polyester sheet may then be cut into the generally rectangular form as illustrated in FIG. 2A, wherein opposing corners 212 are truncated and a central, generally rectangular, region of the bottom layer is also cut away to form an opening 218 therethrough. A reagent film 216 may be deposited over the conductive layer 214 in elongated patterns extending from an interior edge of the central opening 218 to an exterior edge, or outer perimeter, of the bottom layer 210. It will be understood that the reagent film 216 may be deposited onto the conductive layer 214 before or after the bottom layer 210 is cut from the polyester sheet.

With reference to FIG. 2B, a spacer layer 220 may be formed from a sheet of polyester or other non-electrically conductive material such as plastics (PET, PETG, polyimide, polycarbonate, polystyrene), ceramic, glass and the like having adhesive disposed on both sides thereof. The thickness of the spacer layer 220 which defines a spacing for the electrochemical cell of the assembled test strip may vary from about 50 to about 500 microns and usually ranges between about 50 and about 150 microns. According to this specific embodiment, the adhesive-coated polyester spacer layer 220 comprises four symmetrically shaped sections 226 of the polyester, each at about ninety-five (95) microns thick, wherein each section 226 comprises a truncated corner 222 and is spaced apart from an adjacent section 226 to form a channel, or sample chamber 224 there between, when the test strip 200 is fully assembled. The specific dimensions can easily be modified depending on the application. The adhesive coating on both sides of the spacer sections 226 secure the bottom and top layers 230, 210, against the intermediately disposed spacer layer 220. The truncated corners 222 of two of the spacer layer 220 sections 226 are aligned with the two truncated corners of the bottom layer 210, while the sample chambers 224 align with the elongated patterns of the reagent layer 216 on the conductive coating 214 of the bottom layer 210, and an opening 228 in the spacer layer aligns with the opening 218 in the bottom layer 210, when the test strip 200 is assembled.

With reference to FIG. 2C, the top layer 230, which according to this embodiment is formed from a polyester sheet, may have a coating of gold 234 sputtered on one side thereon to form a conductive coating on an inward facing side (after assembly) of the top layer 230. The polyester sheet may then be cut into the generally rectangular form as illustrated in FIG. 2C, wherein opposing corners 232 are truncated and a central, generally rectangular, opening 238 of the top layer 230 is also cut away. Although the reagent film 216 is shown as being deposited on the bottom layer 210, a person skilled in the art will realize that the reagent layer may be deposited only on the conductive surface 234 of the top layer 230 in the same pattern as shown in FIG. 2A, or it may be deposited on both the top and bottom layers, 230, 210, respectively. When the test strip 200 is assembled, as shown in FIG. 2D, the truncated corners 232 of the top layer 230 are assembled adjacent the non-truncated corners of the bottom layer 210, and are aligned with two of the truncated corners 222 of the spacer layer 220. As previously described, an adhesive disposed on both sides of the spacer layer 220 sections 226 secure the top and bottom layers, 230, 210, thereto. The top layer 230 may be fabricated from a transparent polyester sheet such that the sample chambers 224 may be viewable through the transparent top layer 230 and the gold coating 234 thereon.

Referring specifically to FIGS. 2D-2E, the assembled rectangular test strip 200 according to this exemplary embodiment comprises four sample chambers 224, or electrochemical cells, each extending from a sample chamber inlet at one exterior edge (side), or outer perimeter, of the test strip 200 to an interior edge at the central opening 207 of the test strip 200 for receiving a sample applied to one of the inlets by a user of the test meter 10. Each sample chamber 224 is defined by opposing walls comprising the electrodes, or conductive coatings 214, 234, one or both of which may comprise the reagent film deposited thereon which is exposed to the sample applied to the sample chamber 224 for mixing therewith upon contact. Each sample chamber 224 is further defined by opposing walls formed by adjacent spacer sections 226. The assembled test strip 200 comprises contact pads 215, 235, at each corner thereof, and an exposed portion of either the palladium 214 coating on the bottom layer 210, or the gold coating 234 on the top layer 230. By aligning the truncated corners and the non-truncated corners of the top and bottom layers, 230, 210, respectively, during assembly, the conductive metallic layers 214, 234 are exposed to form the contact pads 215, 235, for electrically connecting to flexible metallic conductors, or prongs 206, 208, disposed in the strip port connector 104 of the test meter 10 (not shown in these FIGS.).

Still referring to FIGS. 2D-2E, contact pads 215, facing upward toward the top layer 230, comprise exposed portions of the conductive coating 214 of the bottom layer 210 and are disposed at opposing corners of the test strip 200. Similarly, contact pads 235, facing downward toward the bottom layer 210, comprise exposed portions of the top layer 210 conductive coating 234 and are disposed at opposing corners of the test strip 200. Arrows 240 indicate the four permissible directions for inserting the test strip 200 into the test strip port 22, which may be inserted with either the top or bottom layer 210, 230, facing upward. After insertion of the test strip 200 into the test strip port 22 comprising the strip port connector 104, one of the four inlets of the four sample chambers 224 remains exposed and accessible for receiving a sample therein provided by a user of the test meter 10.

Referring specifically to FIG. 2E, and when there is no test strip inserted into the strip port connector circuit 104, upper and lower conductors of prongs 208 are flexibly biased to electrically contact each other, as well as the upper and lower conductors of the prongs 206. According to this specific embodiment and when the test strip 200 is inserted into the strip port connector circuit 104, the conductive coating 214 of contact pad 215 makes electrical contact with the upper conducting structure of prongs 208 while the conductive coating 234 of contact pad 235 makes electrical contact with the lower conductor of prongs 206. The same electrical contacts are established if the test strip is rotated one-hundred-eighty degrees, in this specific embodiment. In other possible orientations of the test strip 200 in the strip port 22, e.g., rotated ninety degrees or two-hundred seventy degrees, conductive coating 234 of contact pad 235 makes electrical contact with the lower conductor of prong 208 while conductive coating 214 of contact pad 215 makes electrical contact with the upper conductor of prong 206. After insertion of the test strip 24 and application of a sample thereto, a sample assay may be performed as in the normal course of operation. Thus, the strip port connector 104 may transmit an electric signal through the prongs 206, 208, which travel through the conductive films 214, 234, of the upper and lower layers, 230, 210, and through the electrochemical cell formed by the sample provided in one of the four sample chambers 224 which has mixed with the reagent layer therein.

FIGS. 3A-3E illustrate another exemplary embodiment of a substantially flat (planar), rectangular test strip 300 that may be used for analyte measurement in which the herein described test strip 300 may be inserted into a test strip port 22 of the analyte meter 100 in one of at least four (4) orientations. With reference to FIGS. 3A-3C, the test strip 300 is generally defined by three layers herein referred to as a bottom layer 310, a top layer 330, and a spacer layer 320 therebetween, of the fully assembled test strip 300. The top and bottom layers, 330, 310, respectively, may be fabricated from a sheet of polyester or other suitable non-conductive and inert material having a conductive coating sputtered on one side thereof. With respect to the bottom layer 310 according to this embodiment, a palladium coating 314 is sputtered on the sheet of polyester to form the conductive coating on an inward facing side (after assembly) of the bottom layer 310. The polyester sheet may then be cut into the generally rectangular form as illustrated in FIG. 3A, wherein each side edge, or outer perimeter, comprises a notch 312 cut therefrom, and a central, generally rectangular, region of the bottom layer is also cut away to form an opening 318 therethrough. A reagent film 316 may be deposited over the conductive layer 314 in elongated patterns extending from an interior edge, or corner, of the central opening 318 to two opposing exterior edges, or corners, of the bottom layer 310. It will be understood that the reagent film 316 may be deposited onto the conductive layer 314 before or after the bottom layer 310 is cut from the polyester sheet.

With reference to FIG. 3B, a spacer layer 320 may be formed from a sheet of polyester or other suitable inert and structurally supportive material having adhesive disposed on both sides thereof. The polyester spacer layer 320 may comprise two symmetrically shaped sections 326 of the polyester, each at about ninety-five (95) microns thick, wherein each section 326 comprises two notches 322 cut into each of two sides thereof. The two spacer sections 326 are spaced apart to form channels, or sample chambers 324 therebetween, when the test strip 300 is fully assembled. An adhesive coating on both sides of the spacer sections 326 secure the bottom and top layers 330, 310, against the spacer layer 320. One of the notches 322 in each side of the two spacer layer sections 326 is aligned with the notch 312 in each side of the bottom layer 310. The sample chambers 324 align with the elongated patterns of the reagent layer 316 on the conductive coating 314 of the bottom layer 310, and an opening 328 in the spacer layer aligns with the opening 318 in the bottom layer 310, when the test strip 300 is assembled.

With reference to FIG. 3C, the top layer 330, which according to this embodiment is formed from a polyester sheet, may have a coating of gold 334 sputtered on one side thereon to form the conductive coating on an inward facing side (after assembly) of the top layer 330. The polyester sheet may then be cut into the generally rectangular form as illustrated in FIG. 3C, wherein a notch 332 in each side is cut, and a central, generally rectangular, opening 338 of the top layer 330 is also cut away. Although the reagent film 316 is shown as being deposited on the bottom layer 310, a person skilled in the art will realize that a reagent layer may similarly be deposited on the conductive surface 334 of the top layer 330 in the same pattern as shown in FIG. 3A, or reagent layers may be deposited on both the top and bottom layers, 330, 310, respectively. When the test strip 300 is assembled, the notches 332 of the top layer 330 are aligned with one of the notches 322 in each side of the two spacer layer sections 326. As mentioned above, an adhesive disposed on both sides of the sections 326 of the spacer layer 320 secure the top and bottom layers, 330, 310, thereto. The top layer 330 may be fabricated from a transparent polyester sheet such that the sample chambers 324 may be viewable through the transparent top layer 330 and the gold coating 334 thereon.

Referring specifically to FIGS. 3D-3E, the assembled rectangular test strip 300 according to this exemplary embodiment comprises two sample chambers 324, or electrochemical cells, each extending from a sample chamber inlet at one exterior corner of the test strip 300 to an interior corner at the central opening 307 of the test strip 300 for receiving a sample applied to one of the inlets by a user of the test meter 10. Each sample chamber 324 is defined by opposing walls comprising the electrodes, or conductive coatings 314, 334, one or both of which may comprise the reagent film deposited thereon, which is exposed to the sample applied to the sample chamber 324 for mixing therewith upon contact. Each sample chamber 324 is further defined by opposing walls formed by adjacent spacer sections 326. The assembled test strip 300 further comprises two contact pads 315, 335 on each side thereof comprising an exposed portion of the palladium coating 314 on the bottom layer 310 and an exposed portion of the gold coating 334 on the top layer 330. By aligning the notched edges of the spacer layer 320 and the notched edges of the top and bottom layers, 330, 310, respectively, during assembly, the conductive metallic layers 314, 334 are exposed to form the contact pads 315, 335, for electrically connecting to flexible metallic conductors, or prongs 306, 308, disposed in the strip port connector 104 of the test meter 10.

As shown in FIGS. 3D-3E, contact pads 315, facing upward toward the top layer 330, comprise exposed portions of the bottom layer 310 conductive coating 314 and are disposed one at each edge, or outer perimeter, of the rectangular test strip 300. Similarly, contact pads 335, facing downward toward the bottom layer 310, comprise exposed portions of the top layer 310 conductive coating 334 and are also disposed one at each edge, or outer perimeter, of the rectangular test strip 300 forming a pair of contact pads on each of the four sides of the test strip 300. Arrows 340 indicate the four permissible directions for inserting the test strip 300 into the test strip port 22, which may be inserted with either the top or bottom layer 310, 330, facing upward. After insertion of the test strip 300 into the test strip port 22 comprising strip port connector 104, one of two inlets of the two sample chambers 324 remains exposed and accessible for receiving a sample therein provided by a user of the test meter 10.

Referring specifically to FIG. 3E, when there is no test strip inserted into the strip port connector circuit 104, upper and lower conducting structures of prongs 308 are flexibly biased to electrically contact each other, as well as the upper and lower conducting structures of prongs 306. When the test strip 300 is inserted into the strip port connector circuit 104, conductive coating 314 of contact pad 315 makes electrical contact with the upper conductor of prongs 308 while conductive coating 334 of contact pad 335 makes electrical contact with the lower conductor of prongs 306. In another possible orientation of the test strip 300 in the strip port 22, e.g., rotated ninety, one-hundred-eighty, or two-hundred-seventy, degrees, the electrical connections as between prongs 306, 308, and the conductive coatings 314, 334 remains the same. After insertion of the test strip 24 and application of a sample thereto, a sample assay may be performed as in the normal course of operation. Thus, the strip port connector 104 may transmit an electric signal through the prongs 306, 308, which travel through conductive surfaces 314, 334, of the upper and lower layers, 330, 310, and through the electrochemical cell or chamber formed by the sample provided in one of the two sample chambers 324 which has mixed with the reagent layer therein.

Each of the prongs as described herein, 206, 208, 306, 308, comprise flexible spring arms which may be fabricated from a conductive metallic material which flex in a direction away from the test strip 200, 300 when it is inserted into the test strip port 22 by a user of the test meter 10. The prongs 206, 208, 306, 308, may be electrically shorted together absent an inserted test strip therebetween, thereby forming a single circuit node of common voltage. The flexible spring arms provide enough compressive force to make electrical contact with contact pads 215, 235, 315, 335, and to secure the test strip 400 therebetween when the test strip is inserted and when an analyte measurement is being performed by the test meter 10, as described herein.

FIGS. 4A-4E illustrate yet another exemplary embodiment of a substantially flat (planar), circular test strip 400 that may be used for analyte measurement when the test strip 400 is inserted into a test strip port 22 of the analyte meter 100 in either of at least about eight orientations. With reference to FIGS. 4A-4C, the test strip 400 is generally defined by three layers herein referred to as a bottom layer 410, a top layer 430, and a spacer layer 420 therebetween, of the fully assembled test strip 400. The top and bottom layers, 430, 410, respectively, may be fabricated from a sheet of polyester, or other nonconductive material, having a conductive coating sputtered on one side thereof. With respect to the bottom layer 410 and according to this specific embodiment, a palladium coating 414 may be sputtered on the sheet of polyester to form the conductive coating on an inward facing side (after assembly) of the bottom layer 410. The polyester sheet may then be cut into the generally circular form as illustrated in FIG. 4A, wherein a central, generally circular region of the bottom layer is cut away to form an opening 418 therethrough. A reagent film 416 may be deposited over the conductive layer 414 in a plurality of elongated patterns extending radially from an interior edge of the central opening 418 directly to an exterior edge, or outer perimeter, of the bottom layer 410, which may be said to resemble the spokes of a wheel. It will be understood that the reagent film 416 may be deposited onto the conductive layer 414 before or after the bottom circular layer 410 is cut from the polyester sheet.

With reference to FIG. 4B, a spacer layer 420 may be formed from a sheet of polyester or other suitable inert and structurally supportive material having adhesive disposed on both sides thereof. According to this specific embodiment, the polyester spacer layer 420 may comprise about eight symmetrically shaped sections 426 of the polyester, each at about ninety-five (95) microns thick, wherein each section 426 is spaced apart from an adjacent section 426 to form a channel, or sample chamber 424 therebetween, when the test strip 400 is fully assembled. An adhesive coating on both sides of the spacer sections 426 secure the bottom and top layers 430, 410, against the spacer layer 420. The sample chambers 424 align with the elongated patterns of the reagent layer 416 on the conductive coating 414 of the bottom layer 410. The central opening 428 in the spacer layer is positioned such that the opening 418 in the bottom layer 410 is centered in the central opening 428, when the test strip 400 is assembled.

With reference to FIG. 4C, the top layer 430 according to this embodiment includes a sputtered gold coating 434 on one side thereon to form the conductive coating on an inward facing side (after assembly) of the top layer 430. A series of slots 432 are cut through the top layer 430 to permit access therethrough to the conductive coating 414 on the bottom layer 410. The slots may form a generally circular pattern 438 through the top layer 430. A diameter of the circular pattern 438 is larger than a diameter of the central opening 418 in the bottom layer 410 and is smaller or equal to a diameter of the central opening 428 in the spacer layer 420. The polyester sheet may then be cut into the generally circular form as illustrated in FIG. 4C. Although the reagent film 416 is shown as being deposited on the bottom layer 410, a person skilled in the art will realize that the reagent layer 416 may be deposited only on the conductive surface 434 of the top layer 430 in the same pattern as shown in FIG. 4A, or it may be deposited on both the top and bottom layers, 430, 410, respectively. In one embodiment, when the test strip 400 is assembled, the circular pattern 438 of slots 432 in the top layer 430 may be aligned with the sample chambers 424 of the spacer layer 420, which may assist in preventing excessive "wicking" of a sample which may then spill into the opening 428. The conductive coating 414 on the bottom layer 410 is exposed in each of the slots 432 when the assembled test strip 400 is viewed in a direction toward the top side 430, as illustrated in FIG. 4D. When the assembled test strip 400 is viewed in a direction toward its bottom side 410, the conductive coating 434 on the top side 430 is exposed in the opening 418 in the bottom side 410, as illustrated in FIG. 4E. As mentioned above, an adhesive disposed on both sides of the spacer layer 420 sections 426 secure the top and bottom layers, 430, 410, respectively, thereto. The top layer 430 may be fabricated from a transparent polyester sheet such that the sample chambers 424 may be viewable through the transparent top layer 430 and the gold coating 434 thereon.

Referring specifically to FIGS. 4D-4E, the assembled circular test strip 400 according to this specific embodiment comprises eight sample chambers 424, or electrochemical cells, each extending from a sample chamber inlet at an exterior edge, or outer perimeter, of the circular test strip 400 toward a center of the test strip 400 for receiving a sample applied to one of the inlets by a user of the test meter 10. Each of the sample chamber 424 inlets at the exterior edge, or outer perimeter, of the test strip 400 are substantially equally spaced from each other along the exterior edge, or outer perimeter. In the exemplary embodiment shown in FIGS. 4D-4E, the test strip 400 comprises eight sample chambers 424. Each sample chamber 424 is defined by opposing walls comprising the electrodes, or conductive coatings 414, 434, one or both of which may comprise the reagent film 416 deposited thereon, which is exposed to the sample applied to the sample chamber 424 for mixing therewith upon contact. Each sample chamber 424 is further defined by opposing walls formed by adjacent spacer sections 426. In an alternative embodiment, a plurality of openings, or holes 436, one example of which is illustrated in FIGS. 4D-4E, may be formed through the test strip 400, such as by a punch tool directly through each of the sample chambers 424 at one end of the sample chambers 424 proximate the slots 432. Such holes 436 may help prevent leakage of a provided sample onto the contact pad 435 and may ensure consistent volumes across all of the sample chambers 424.

By aligning the exterior edges of the three layers 410-430 during assembly, the conductive coatings 414, 434 may be exposed to form the contact pads 415, 435, for electrically connecting to prongs disposed in the strip port connector 104 of the test meter 10. Thus, the assembled test strip 400 comprises eight contact pads 415 accessible from a top side of the assembled test strip 400 through the eight slots 432, as illustrated in FIG. 4D, each comprising an exposed portion of the palladium 414 coating on the bottom layer 410. Flexible metallic prongs may be disposed in a strip port connector 104 of the test meter 10 to make electrical contact with at least one of the contact pads 415 when the test strip is inserted therein in any of about eight different orientations as indicated by the arrows 440. The prongs may be configured to include two side-by-side (adjacent) conductors so that at least one of the conductors will avoid the gap between adjacent slots 432 and engage one of the contact pads 415 inside a corresponding slot 432. The prongs comprising such side-by-side conductors enable the circular test strip 400 to be inserted into the test strip port 22 in substantially any orientation, and is not limited to the eight orientations indicated by the arrows 440. The assembled test strip 400 comprises a contact pad 435 accessible from a bottom side of the assembled test strip 400 through the central opening 418 of the bottom layer 410, as illustrated in FIG. 4E, comprising an exposed portion of the gold coating 434 on the top layer 430. At least one flexible metallic prong may be disposed in a strip port connector 104 of the test meter 10 to make electrical contact with the contact pad 435 when the test strip is inserted in any orientation because the central location of the contact pad 435 does not vary with orientation of the test strip 400.

After insertion of the test strip 400 into the test strip port 22 comprising strip port connector 104, at least one inlet of the eight sample chambers 424 remains exposed and accessible for receiving a sample therein provided by a user of the test meter 10. After application of a sample thereto, a sample assay may be performed as in the normal course of operation. Thus, the strip port connector 104 may transmit an electric signal through prongs electrically connected to contact pads 415, 435, which travel through conductive surfaces 414, 434, of the upper and lower layers, 430, 410, respectively, and through electrochemical cell formed by the sample provided in one of eight sample chambers 424, which sample has mixed with the reagent layer 416 therein.

A person skilled in the art will appreciate that the test strip embodiments 200, 300, 400, described herein can have various configurations other than those shown, and may include any combination of features disclosed herein and known in the art. For example, the test strip may comprise any shape in the form of a regular polygon having a number of sides other than the rectangular four-sided embodiments described herein, such as triangular, hexagonal, octagonal, etc. Moreover, each test strip 200, 300, 400 may include a sample chamber at various locations for measuring the same (glucose) and/or different analytes in a sample.

The test strip 200, 300, 400 may have various configurations, but it is typically in the form of rigid, semi-rigid, or flexible layers having sufficient structural integrity to allow handling and connection to an analyte measurement system 100. It should be noted that, as used herein, the term "rectangular" includes square shaped configurations. In all the embodiments disclosed herein, the test strip layers may be formed from various inert support or backing material other than the polyester embodiments described herein, including plastic, polymeric, or other materials as described herein with reference to FIGS. 2A-2E. The material of the test strip layers typically is one that is insulating (non-conductive) and may be inert and/or electrochemically non-functional, where they do not readily corrode over time nor chemically react with a sample applied to the sample chamber of the test strip. The conductive layer, or coating, on the top and bottom nonconductive layers may include sputtered metallic coatings other than gold and palladium, as described herein with reference to FIGS. 2A-2E, and may comprise conductive sheets adhered to the nonconductive top and bottom layers, such as a sheet of metallic foil. The conductive layers, or coating, should also be resistant to corrosion wherein their conductivity does not change during storage of the test strip. The conductive layers may be adulterated with a suitable material that aids filling of the pre-formed sample chamber with essentially aqueous-based samples of biological origin, e.g., mercaptoethane sulphonic acid and the like. Similarly, the spacer layer as formed in exemplary test strip embodiments 200, 300, 400 may have various configurations, thicknesses, and may be formed from a sheet of polyester or other non-electrically conductive material such as plastics (PET, PETG, polyimide, polycarbonate, polystyrene), ceramic, glass and the like having adhesive disposed on both sides thereof, as described with reference to FIG. 2B described herein.

As will be appreciated by one skilled in the art, aspects of the present invention may be embodied as a processing system, method, or apparatus. Accordingly, aspects of the present invention may take the form of an entirely hardware embodiment, an entirely software embodiment (including firmware, resident software, micro-code, etc.), or an embodiment combining software and hardware aspects that may all generally be referred to herein as a "circuit," "circuitry," "module," 'subsystem" and/or "system." Furthermore, aspects of the present invention may take the form of a computer program product embodied in one or more computer readable medium(s) having computer readable program code embodied thereon.

Program code and/or data representative of operations and measurements performed may be stored using any appropriate medium, including but not limited to any combination of one or more computer readable medium(s). A computer readable storage medium may be, for example, an electronic, magnetic, optical, electromagnetic, infrared, or semiconductor system, apparatus, or device, or any suitable combination of the foregoing. More specific examples of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible, non-transitory medium that can contain, or store a program for use by or in connection with an instruction execution system, apparatus, or device.

Program code and/or data representative of operations and measurements performed may be transmitted using any appropriate medium, including but not limited to wireless, wireline, optical fiber cable, RF, etc., or any suitable combination of the foregoing.

PARTS LIST FOR FIGS. 1A-4E

10 analyte meter
11 housing, meter
13 data port
14 display
16 user interface buttons
22 test strip port
24 test strip
100 analyte measurement system
101 memory module
102 keypad (buttons) module
103 user interface module
104 strip port connector
105 microcontroller settings module
106 transceiver module
107 antenna
108 WiFi module
109 Bluetooth module
110 NFC module
111 GSM module
112 RAM module
113 ROM module
114 external storage
115 light source module
116 power supply module
117 AC power supply
118 battery power supply
119 display module
120 audio module
121 speaker
122 microcontroller (processing unit)
123 communication interface
125 analog front end subsystem
140 data management unit
200 test strip
206 prongs
207 opening, test strip
208 prongs
210 bottom layer
212 bottom layer corners, truncated
214 palladium coating
215 contact pad
216 reagent layer
218 opening, bottom layer
220 spacer layer
222 spacer layer corners, truncated
224 sample chamber
226 spacer sections
228 opening, spacer layer
230 top layer 232 top layer corners, truncated
234 gold coating
235 contact pad
238 opening, top layer
240 arrows, insertion direction
300 test strip
306 prongs
307 opening, test strip
308 prongs
310 bottom layer
312 notches, bottom layer
314 palladium coating
315 contact pad
316 reagent layer
318 opening, bottom layer
320 spacer layer
322 notches, spacer layer
324 sample chamber
326 spacer sections
328 opening, spacer layer
330 top layer
332 notches, top layer
334 gold coating
335 contact pad
338 opening, top layer
340 arrows, insertion direction
400 test strip
410 bottom layer
414 palladium coating
415 contact pad
416 reagent layer
418 opening, bottom layer
420 spacer layer
424 sample chamber
426 spacer sections
428 opening, spacer layer
430 top layer
432 arced slots
434 gold coating
435 contact pad
436 opening, test strip
438 circular pattern
440 arrows, insertion direction While the invention has been described in terms of particular variations and illustrative figures, those of ordinary skill in the art will recognize that the invention is not limited to the variations or figures described. In addition, where methods and steps described above indicate certain events occurring in certain order, those of ordinary skill in the art will recognize that the ordering of certain steps may be modified and that such modifications are in accordance with the variations of the invention. Additionally, certain of the steps may be performed concurrently in a parallel process when possible, as well as performed sequentially as described above. Therefore, to the extent there are variations of the invention, which are within the spirit of the disclosure or equivalent to the inventions found in the claims, it is the intent that this patent will cover those variations as well.

What is claimed is:

1. A multi-orientation test strip comprising:
a first layer having a first conductive surface;
a second layer having a second conductive surface, the second conductive surface facing the first conductive surface; and
a spacer layer disposed between the first and second layers, the spacer layer comprising a plurality of spacer sections arranged to form a plurality of adjacent sample chambers having a plurality of corresponding sample chamber inlets formed at exterior edges of the test strip, each of the sample chamber inlets in fluid communication with a corresponding one of the sample chambers,
wherein the sample chambers extend between an exterior edge and an interior edge of the test strip,
wherein the first layer, the second layer, and the spacer layer are each substantially circular in shape and in which the layers are assembled to form a substantially circular test strip,
wherein the sample chamber inlets are each equally spaced along an exterior edge of the test strip, and
wherein the first layer comprises a central opening of a first diameter, the second layer comprises a plurality of curved openings delineating a circular pattern, the circular pattern having a second diameter larger than the first diameter, and wherein the spacer layer comprises a plurality of portions disposed radially at the outside edge of the test strip to form the sample chamber inlets, such that the first conductive layer is exposed through the plurality of curved openings in the second layer, and the second conductive layer is exposed through the central opening in the first layer, when the test strip is assembled.

2. The multi-orientation test strip of claim 1, wherein the spacer layer is adhered to the first and second conductive surfaces.

3. The multi-orientation test strip of claim 1, wherein the first layer comprises a transparent polyester layer, and wherein the sample chambers are visible through the first polyester layer.

* * * * *